United States Patent [19]

Dominianni et al.

[11] Patent Number: 4,609,670

[45] Date of Patent: Sep. 2, 1986

[54] IMIDAZOLIUM HYPOGLYCEMIC AGENTS

[75] Inventors: Samuel J. Dominianni; Terence T. Yen, both of Indianapolis, Ind.

[73] Assignee: Eli Lilly and Company, Indianapolis, Ind.

[21] Appl. No.: 670,776

[22] Filed: Nov. 13, 1984

[51] Int. Cl.$^4$ ............................................. A61K 31/415
[52] U.S. Cl. ..................................... 514/399; 548/341
[58] Field of Search ........................................ 514/399

[56] References Cited

U.S. PATENT DOCUMENTS

| | | | |
|---|---|---|---|
| 3,852,301 | 12/1974 | Haugwitz et al. | 548/341 |
| 4,017,631 | 4/1977 | Janssen et al. | 514/399 |
| 4,243,670 | 1/1981 | Regel et al. | 548/341 X |
| 4,251,540 | 2/1981 | Regel et al. | 514/396 |

FOREIGN PATENT DOCUMENTS

| | | | |
|---|---|---|---|
| 54-079278 | 6/1979 | Japan | 548/341 |
| 54-79278 | 6/1979 | Japan | 548/341 |
| 58-150567 | 9/1983 | Japan | 548/341 |

OTHER PUBLICATIONS

Boekelheide, V. et al., *J. Am. Chem. Soc.*, 90, 14, 3830, (1968).
Nardi, D. et al., *J. Med. Chem.*, 24, 727–731, (1981).
Schütze, D. et al., *Justus Liebigs Ann. Chem.* 765, 29–33, (1972).
Jones, J. et al., *Can. J. Chem.*, 49(2), 325–332, (1971).
Lown, J. et al., *Can. J. Chem.*, 53(24), 3782–3790, (1975).
Tsuge, O. et al., *Bull. Chem. Soc. Jpn.*, 56, 2073–2076, (1983).
Rudenko, A. et al., *J. Prakt. Chem.* 325(4), 627–641, (1983).

*Primary Examiner*—Richard A. Schwartz
*Attorney, Agent, or Firm*—Bruce J. Barclay; Arthur R. Whale

[57] ABSTRACT

Imidazolium salts are effective in lowering blood glucose levels in mammals following administration.

18 Claims, No Drawings

IMIDAZOLIUM HYPOGLYCEMIC AGENTS

BACKGROUND OF THE INVENTION

Diabetes mellitus is a systemic disease characterized by disorders in the metabolism of insulin, carbohydrates, fats, and proteins, and in the structure and function of blood vessels. There are several causes of the disease including a large genetic component as well as a relationship to the type and amount of physical exercise and diet of the individual. The primary symptom of acute diabetes mellitus is hyperglycemia, often accompanied by glucosuria, the presence in urine of abnormal amounts of glucose, and polyuria, the excretion of large volumes of urine. Additional symptoms arise in chronic or long-standing diabetes. These include degeneration of the walls of blood vessels. Although many different organs are affected by these vascular changes, the eyes appear to be the most susceptible. As such, long-standing diabetes mellitus, even when treated with insulin, is a leading cause of blindness.

There are two recognized types of diabetes. Juvenile onset, or ketosis-prone, diabetes develops early in life with much more severe symptoms, and has a near-certain prospect of later vascular involvement. Control of this type of diabetes is often difficult. The second type of diabetes is adult onset, or ketosis-resistant, diabetes. This form develops later in life, is milder and has a more gradual onset.

One of the most significant advancements in the history of medical science came in 1922 when Banting and Best demonstrated the therapeutic affects of insulin in diabetic humans. However, even today, a clear picture of the basic biochemical defects of the disease is not known, and diabetes is still a serious health problem. It is believed that two percent or more of the population of the United States is afflicted with some form of diabetes.

The introduction of orally effective hypoglycemic agents was also an important development in the treatment of diabetes mellitus. Hypoglycemic agents are useful in the treatment of hyperglycemia by lowering blood glucose levels. The term "hyperglycemia" refers to a clinical condition resulting from an abnormally high blood glucose level. Oral hypoglycemic agents are normally used in the treatment of adult onset diabetes since older individuals have a better chance of recovery than an individual afflicted with juvenile onset diabetes.

The present invention relates to a new class of orally active hypoglycemic agents capable of lowering blood glucose levels in mammals with adult onset diabetes.

SUMMARY OF THE INVENTION

The present invention relates to a method for lowering blood glucose levels in mammals comprising administering an effective amount of a compound of the formula

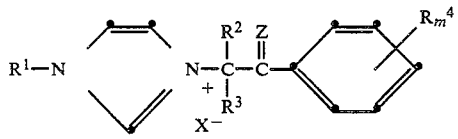

wherein:
$R^1$ is $C_1$-$C_4$ alkyl;
$R^2$ and $R^3$ independently are hydrogen or $C_1$-$C_4$ alkyl,
each $R^4$ independently is —$OR^5$, —$NR^6R^7$, $C_1$-$C_4$ alkyl, $C_1$-$C_4$ alkoxy or $C_1$-$C_4$ alkylthio;
$R^5$ is hydrogen or

$R^6$ is hydrogen, $C_1$-$C_4$ alkyl or

$R^7$ is hydrogen or $C_1$-$C_4$ alkyl;
each $R^8$ independently is $C_1$-$C_4$ alkyl or phenyl;
Z is oxygen or sulfur;
X is a therapeutically acceptable anion; and
m is 0, 1 or 2.

The present invention also provides a pharmaceutical formulation comprising a compound of formula I and a pharmaceutically acceptable carrier, diluent or excipient therefore. The present invention also provides a compound of the formula

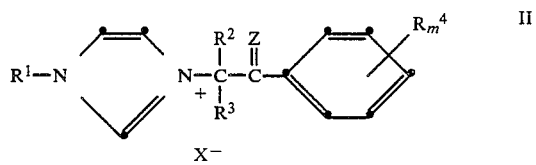

wherein:
$R^1$ is $C_1$-$C_4$ alkyl;
$R^2$ and $R^3$ independently are hydrogen or $C_1$-$C_4$ alkyl;
each $R^4$ independently is —$OR^5$, $NR^6R^7$, $C_1$-$C_4$ alkyl, $C_1$-$C_4$ alkoxy or $C_1$-$C_4$ alkylthio;
$R^5$ is hydrogen or

$R^6$ is hydrogen, $C_1$-$C_4$ alkyl or

$R^7$ is hydrogen or $C_1$-$C_4$ alkyl;
each $R^8$ independently is $C_1$-$C_4$ alkyl or phenyl;
Z is oxygen or sulfur;
X is a therapeutically acceptable anion; and
m is 0, 1 or 2;
with the provisos that when $R^1$ is methyl, $R^2$ and $R^3$ are hydrogen and Z is oxygen, m is other than 0; when $R^1$ is methyl, $R^2$ and $R^3$ are hydrogen, Z is oxygen, and X is bromine, $R^4$ is other than 4-methoxy and 4-methyl.

DETAILED DESCRIPTION OF THE INVENTION

All temperatures stated herein are in degrees Celsius. All units of measurement employed herein are in weight units except for liquids, which are in volume units.

As used herein, the term $C_1$-$C_4$ alkyl represents a straight or branched alkyl chain having from one to four carbon atoms. Typical $C_1$-$C_4$ alkyl groups include methyl, ethyl, n-propyl, isopropyl, n-butyl, sec.-butyl, isobutyl and t-butyl.

$C_1-C_4$ Alkoxy represents a straight or branched alkoxy chain having from one to four carbon atoms. Typical $C_1-C_4$ alkoxy groups include methoxy, ethoxy, n-propoxy, isopropoxy, n-butoxy, sec.-butoxy, isobutoxy and t-butoxy.

$C_1-C_4$ Alkylthio represents a straight or branched alkylthio chain having from one to four carbon atoms. Typical $C_1-C_4$ alkylthio groups include methylthio, ethylthio, n-propylthio, sec.-butylthio and the like.

The compounds employed in this invention are imidazolium salts and as such require a therapeutically acceptable anion, defined in the above formula by "$X^-$". Any suitable anion which goes together with the imidazolium cation to form a therapeutically acceptable salt can be utilized. Commonly used anions include chloride, bromide, iodide, sulfonate, p-toluenesulfonate, methanesulfonate, p-bromophenylsulfonate, phosphate, carbonate, oxalate, succinate, citrate, benzoate, acetate, and the like. A preferred and commonly used anion is bromide. Another preferred anion is chloride.

The following list of imidazolium salts is illustrative of the compounds comprehended for use according to the present invention.

1-Ethyl-3-[2-(4-methylphenyl)-2-oxoethyl]-1H-imidazolium bromide
1-Methyl-3-[2-(2,4-dimethylphenyl)-2-oxoethyl]-1H-imidazolium chloride
1-Methyl-3-[2-(2-ethyl-4-methoxyphenyl)-2-oxoethyl]-1H-imidazolium bromide
1-Methyl-3-[2-(4-methylphenyl)-2-oxoethyl]-1H-imidazolium chloride
1-Methyl-3-[2-(3-methoxyphenyl)-2-oxoethyl]-1H-imidazolium chloride
1-sec.-Butyl-3-(2-phenyl-2-oxoethyl)-1H-imidazolium bromide
1-Methyl-3-[2-(3-methoxyphenyl)-2-oxoethyl]-1H-imidazolium iodide
1-n-Propyl-3-[2-(4-methylphenyl)-2-oxoethyl]-1H-imidazolium bromide
1-Methyl-3-[2-(4-methylphenyl)-2-oxoethyl]-1H-imidazolium sulfonate
1-Methyl-3-[2-(4-methylphenyl)-2-oxoethyl]-1H-imidazolium methanesulfonate
1-Methyl-3-[2-(3-methylphenyl)-2-oxoethyl]-1H-imidazolium phosphate
1-Methyl-3-[2-(4-n-butylphenyl)-2-oxoethyl]-1H-imidazolium iodide
1-sec.-Butyl-3-[2-(3,5-diethoxyphenyl)-2-oxoethyl]-1H-imidazolium chloride
1-Methyl-3-[2-(4-methylphenyl)-2-oxoethyl]-1H-imidazolium bromide
1-Methyl-3-[2-(3,4-dihydroxyphenyl)-2-oxoethyl]-1H-imidazolium bromide
1-t-Butyl-3-[2-(4-aminophenyl)-2-oxoethyl]-1H-imidazolium chloride
1-Methyl-3-(1-n-propyl-2-phenyl-2-oxoethyl)-1H-imidazolium bromide
1-Methyl-3-[2-(4-n-propoxyphenyl)-2-oxoethyl]-1H-imidazolium bromide
1-Methyl-3-[1-methyl-2-(4-methylphenyl)-2-oxoethyl]-1H-imidazolium succinate
1-Methyl-3-[2-(4-methylphenyl)-2-thioxoethyl]-1H-imidazolium bromide
1-Methyl-3-[2-(2,6-dimethylphenyl)-2-oxoethyl]-1H-imidazolium iodide While all combinations of variables listed in the above formulas provide compounds having the ability to lower blood glucose in mammals, there are preferred compounds for such use. For example, $R^1$ is preferably methyl and $R^2$ and $R^3$ are preferably methyl or hydrogen. $R^2$ and $R^3$ are especially both hydrogen. Other preferred aspects of the compounds employed in the present invention will be noted hereinafter.

A preferred procedure used to prepare the compounds of this invention involves reacting a 1-alkylimidazole with a phenacyl derivative. This reaction may be represented by the following scheme:

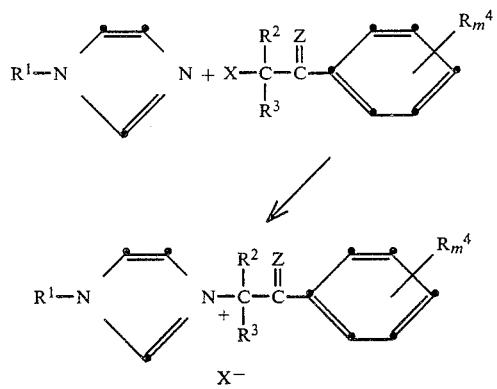

wherein $R^1$, $R^2$, $R^3$, $R^4$, Z, X and m are as defined above.

This process is carried out by simply combining an appropriate phenacyl derivative with an equimolar or slight excess amount of a 1-alkylimidazole in a mutual solvent. Typical solvents suitable for use in this process should be aprotic and include tetrahydrofuran, dimethylsulfoxide, dimethylformamide, sulfolane, 1,2-dimethoxyethane, diethyl ether, and preferably acetonitrile. The reaction is substantially complete after about 1 to 72 hours when conducted at a temperature in the range of about 0° C. to about 150° C. The reaction is preferably conducted at a temperature in the range of about 20° C. to about 35° C. for about 1 to 24 hours. The product may be isolated by procedures well known in the art. Either the precipitated solid is collected by filtration or the reaction solvents are removed by evaporation or decantation. The product may be further purified if desired by common techniques such as crystallization or chromatography over solid supports such as silica gel or alumina.

Thioxoethyl imidazolium compounds defined by the above general formula wherein E is sulfur form another important group of compounds that are orally active hypoglycemic agents and are a further embodiment of this invention. The thioxoethyl compounds of the invention are preferably prepared by thiating the corresponding phenacyl derivative according to the following scheme:

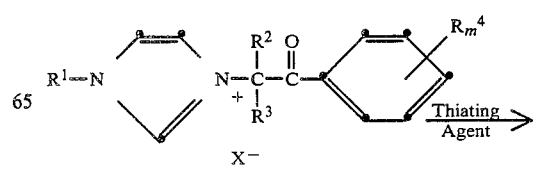

-continued

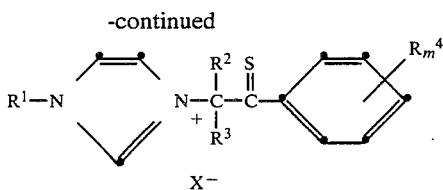

wherein $R^1$, $R^2$, $R^3$, $R^4$, X and m are as defined above.

Any of several thiating agents can be employed in this reaction including phosphorous pentasulfide. Another preferred thiating agent is Lawesson's Reagent, which is 2,4-bis(4-methoxyphenyl)-1,3-dithia-2,4-diphosphetane-2,4-disulfide. This thiating agent and its general uses are described in detail in *Tetrahedron Letters*, 21, 4061 (1980). The thiation reaction is preferably carried out by combining approximately equimolar quantities of the phenacyl compound and Lawesson's Reagent in a mutual organic solvent such as toluene or dioxane. The reaction is generally complete within about 1 hour to about 10 hours when carried out at a temperature of about 50° C. to about 150° C. The compound thus formed can be isolated and purified by normal methods such as crystallization and the like.

The compounds employed in the present invention may be prepared by alternative syntheses as well. For example, an appropriate 1-phenacyl imidazole derivative may be reacted with an alkyl halide to afford the corresponding 1-alkyl-3-phenacyl imidazolium derivative. Also, compounds of formula I wherein Z is oxygen may be readily prepared by treating imidazole with a phenyl epoxide to give the corresponding 1-(2-hydroxy-2-phenylethyl)imidazole. This compound may then be either oxidized to the ketone and reacted with an alkyl halide, or reacted with an alkyl halide and then oxidized to the ketone to provide the corresponding 1-alkyl-3-phenacyl imidazolium salt of the invention. Each of the above described procedures may be conducted by standard procedures well known to one of ordinary skill in the art.

Compounds wherein $R^4$ is hydroxy are preferably prepared by first protecting the substituent, for example with an alkyl group to afford an alkoxy moiety, and then removing the protecting group, for example with a strong acid such as hydrogen bromide, or with a more mild reagent such as iodotrimethylsilane.

Compounds of formula I wherein the hydroxy or amino substituent on the phenyl ring contains an acyl or benzoyl moiety are also prepared by general processes. The acylated compounds are prepared by standard acylation conditions at any of the stages in the synthesis of the final products according to the procedures described above.

The therapeutically acceptable anion associated with the imidazolium cationic portion of the salts employed in this invention is defined in the above formula by $X^-$. It should be recognized that the particular anion forming a part of any salt of this invention is not of a critical nature, so long as the salt as a whole is pharmacologically acceptable and as long as the anionic moiety does not contribute numerous undesired qualities to the salt as a whole. Preferred anions to be utilized are the halides, and whenever a halide such as chloride or bromide is the anion portion of the salt, it can, if desired for any reason, be readily replaced by a different anion. Such replacement can be effected either directly by metathesis, i.e., by double decomposition either in solution or by employing anion exchange resin, or alternatively by conversion of the quaternary salt to the corresponding hydroxide, and then neutralization of the hydroxide by reaction with the appropriate acid. For example, an imidazolium halide can be passed over a hydroxide ion exchange resin, or reacted with aqueous silver oxide, to form the corresponding imidazolium hydroxide. Reaction of the hydroxide with an acid such as methanesulfonic acid, formic acid, butyric acid, nitric acid, phosphoric acid or the like, then provides the imidazolium salt having an anion corresponding to the acid utilized.

The starting materials used to prepare the compounds employed in the present invention are either commercially available or readily prepared by known processes. For example, the phenacyl starting materials wherein X is halide may be readily synthesized by treating an acetophenone derivative with a halogenating agent, such as bromine or iodine, in methylene chloride and acetic acid at a temperature in the range of about 0° C. to about 25° C.

The following Examples further illustrate specific aspects of the present invention. The Examples are not intended to be limiting to the scope of compounds employed in the invention in any respect and should not be so construed.

EXAMPLE 1

1-Methyl-3-[2-(4-methylphenyl)-2-oxoethyl]-1H-imidazolium bromide

To a solution of 10.6 g (0.05 mol) of 1-bromo-2-(4-methylphenyl)-2-oxoethane in 150 ml of diethyl ether was added 4.18 g (0.051 mol) of 1-methylimidazole (Aldrich Chemical Company, Milwaukee, Wis.). The reaction mixture was stirred for approximately 3 hours at room temperature and the precipitated solid was collected by filtration. The resulting hygroscopic solid was recrystallized from methanol/ethyl acetate to afford 4.82 g of 1-methyl-3-[2-(4-methylphenyl)-2-oxoethyl]-1H-imidazolium bromide as a solid. A second crop was obtained from the filtrate to provide an additional 5.8 g of product. (72% yield) mp=148°–151° C.

Analysis calculated for $C_{13}H_{15}BrN_2O$. Theory: C, 52.90; H, 5.12; N, 9.49; Found: C, 52.73; H, 4.95; N, 9.26.

EXAMPLE 2

1-Methyl-3-[2-(3-methoxyphenyl)-2-oxoethyl]-1H-imidazolium bromide

A solution of 4.58 g (0.02 mol) of 1-bromo-2-(3-methoxyphenyl)-2-oxoethane in 100 ml of diethyl ether was filtered, and the filtrate was treated with 1.82 g (0.022 mol) of 1-methylimidazole. The resulting reaction mixture was stirred at room temperature for approximately 19 hours whereupon the solution was decanted and the residue was washed with diethyl ether. The residue was dissolved in hot acetonitrile and, upon cooling, dark needles precipitated out of solution. The resulting solid was collected and recrystallized twice from acetonitrile/ethyl acetate to afford 2.1 g of 1-methyl-3-[2-(3-methoxyphenyl)-2-oxoethyl]-1H-imidizolium bromide as white needles. (34% yield) mp=167°–171° C.

Analysis calculated for $C_{13}H_{15}BrN_2O_2$. Theory: C, 50.18; H, 4.86; N, 9.00; Br, 25.68; Found: C, 49.89; H, 4.75; N, 8.98; Br, 25.56.

EXAMPLE 3

1-Methyl-3-[2-(3-ethoxyphenyl)-2-oxoethyl]-1H-imidazolium bromide

A solution of 2.9 g (0.012 mol) of 1-bromo-2-(3-ethoxyphenyl)-2-oxoethane in 20 ml of acetonitrile was combined with 1.03 g (0.013 mol) of 1-methylimidazole and the resulting mixture was stirred at room temperature for approximately 18 hours. The mixture was diluted with methanol and the volatiles were evaporated under reduced pressure to a volume of approximately 15 ml. This solution was diluted with ethyl acetate and the precipitated brown solid was collected by filtration. The collected solid was washed with ethyl acetate and dissolved in hot acetonitrile. The mixture was purified with charcoal and upon cooling the solid was collected. The solid was recrystallized from acetonitrile/diethyl ether to provide two crops which were combined and recrystallized three times from isopropyl alcohol to afford 0.27 g of 1-methyl-3-[2-(3-ethoxyphenyl)-2-oxoethyl]-1H-imidazolium bromide as pale yellow flakes. (7% yield) mp=137°-138° C.

Analysis calculated for $C_{14}H_{17}BrN_2O_2$. Theory: C, 51.71; H, 5.27; N, 8.61; Br, 24.57; Found: C, 51.54; H, 5.01; N, 8.40; Br, 24.80.

EXAMPLE 4

1-Methyl-3-(1,1-dimethyl-2-phenyl-2-oxoethyl)-1H-imidazolium bromide

A solution of 4.6 g (0.02 mol) of α-bromoisobutyrophenone and 1.8 g (0.022 mol) of 1-methylimidazole in 30 ml of diethyl ether was stirred at room temperature for approximately 48 hours. The solvent was decanted and the resulting oil was slurried in ethyl acetate. The solvent was again decanted and the residue was dissolved in acetonitrile prior to adding a small portion of ethyl acetate. A white precipitate was collected by filtration and recrystallized from methanol/ethyl acetate to afford 3.88 g of 1-methyl-3-(1,1-dimethyl-2-phenyl-2-oxoethyl)-1H-imidazolium bromide as glittering white flakes. (63% yield) mp=137°-140° C.

Analysis calculated for $C_{14}H_{17}BrN_2O$. Theory: C, 54.38; H, 5.54; N, 9.06; Br, 25.84; Found: C, 54.25; H, 5.82; N, 8.87; Br, 25.67.

EXAMPLE 5

1-Methyl-3-[2-(4-ethylphenyl)-2-oxoethyl]-1H-imidazolium bromide

A solution of 4.41 g (0.019 mol) of 1-bromo-2-(4-ethylphenyl)-2-oxoethane and 1.65 g (0.02 mol) of 1-methylimidazole in 40 ml of diethyl ether was stirred at room temperature for approximately 18 hours. The reaction solvent was decanted, and the residue was washed with diethyl ether and dissolved in a small amount of acetonitrile. The resulting solution was diluted with a small amount of ethyl acetate, whereupon a brown precipitate formed. The solid was collected and recrystallized from acetonitrile/ethyl acetate to provide 2.26 g of 1-methyl-3-[2-(4-ethylphenyl)-2-oxoethyl]-1H-imidazolium bromide as fine yellow brown needles. (38% yield) mp=177°-179° C.

Analysis calculated for $C_{14}H_{17}BrN_2O$. Theory: C, 54.38; H, 5.54; N, 9.06; Br, 25.84; Found: C, 54.13; H, 5.81; N, 9.04; Br, 26.05.

EXAMPLE 6

1-Methyl-3-[2-(2-methylphenyl)-2-oxoethyl]-1H-imidazolium bromide

A solution of 4.22 g (0.02 mol) of 1-bromo-2-(2-methylphenyl)-2-oxoethane, 2.64 g (0.032 mol) of 1-methylimidazole and 60 ml of diethyl ether was stirred at room temperature for approximately 17 hours. The reaction solvent was decanted and the residue was washed with diethyl ether. The residue was dissolved in hot acetonitrile, and the resulting solution was cooled and diluted with diethyl ether. The solid was collected and recrystallized twice from acetonitrile/diethyl ether to afford 1.99 g of 1-methyl-3-[2-(2-methylphenyl)-2-oxoethyl]-1H-imidazolium bromide as white needles. (34% yield) mp=152°-154° C.

Analysis calculated for $C_{13}H_{15}BrN_2O$. Theory: C, 52.90; H, 5.12; N, 9.49; Br, 27.07; Found: C, 52.82; H, 5.28; N, 9.54; Br, 27.14.

EXAMPLE 7

1-Methyl-3-(1-methyl-2-phenyl-2-oxoethyl)-1H-imidazolium bromide

A solution of 8 ml (0.047 mol) of 90% pure 1-phenyl-1-oxo-2-bromopropane and 4.25 g (0.052 mol) of 1-methylimidazole in 100 ml of diethyl ether was stirred at room temperature for approximately 24 hours. The precipitated solid was collected by filtration, washed with diethyl ether and dissolved in methanol. This solution was diluted with diethyl ether and the resulting white solid was collected by filtration. This solid was recrystallized from methanol/diethyl ether to afford 7.65 g of 1-methyl-3-(1-methyl-2-phenyl-2-oxoethyl)-1H-imidazolium bromide as white crystals. (55% yield) mp=167°-170° C.

Analysis calculated for $C_{13}H_{15}BrN_2O$. Theory: C, 52.90; H, 5.12; N, 9.49; Found: C, 52.73; H, 4.95; N, 9.26;

EXAMPLE 8

1-Methyl-3-[1-methyl-2-(4-methylphenyl)-2-oxoethyl]-1H-imidazolium bromide

A solution 2.24 g (0.01 mol) of 1-(4-methylphenyl)-1-oxo-2-bromopropane and 0.9 g (0.011 mol) of 1-methylimidazole in 50 ml of diethyl ether was stirred at room for approximately 18 hours. The reaction solvent was decanted, and the residue was washed with diethyl ether and dissolved in acetonitrile. The resulting solution was diluted with diethyl ether and the precipitated solid was collected by filtration. The solid was recrystallized from acetonitrile/diethyl ether to afford 0.33 g of 1-methyl-3-[1-methyl-2-(4-methylphenyl)-2-oxoethyl]-1H-imidazolium bromide as a solid. (11% yield) mp=175°-177° C.

Analysis calculated for $C_{14}H_{17}BrN_2O$. Theory: C, 54.38; H, 5.54; N, 9.06; Found: C, 54.09; H, 5.54; N, 9.17.

A second crop was obtained from the filtrate to provide an additional 0.4 g of the title product. mp=174°-178° C.

EXAMPLE 9

1-Methyl-3-[2-(2,4-dimethylphenyl)-2-oxoethyl]-1H-imidazolium bromide

A solution of 4.76 g (0.021 mol) of 1-bromo-2-(2,4-dimethylphenyl)-2-oxoethane and 1.76 g (0.021 mol) of 1-methylimidazole in 50 ml of diethyl ether was stirred at room temperature for approximately 21 hours. The reaction solvent was decanted and the residue was washed with diethyl ether. The residue was recrystallized from acetonitrile/ethyl acetate to afford 3.32 g of the title product as white crystals. (51% yield) mp=179°–181° C.

Analysis calculated for $C_{14}H_{17}BrN_2O$. Theory: C, 54.38; H, 5.54; N, 9.09; Br, 25.84; Found : C, 54.18; H, 5.46; N, 8.86; Br, 25.96.

EXAMPLE 10

1-Methyl-3-[2-(3-methylphenyl)-2-oxoethyl]-1H-imidazolium bromide

A solution of 5.16 g (0.024 mol) of 1-bromo-2-(3-methylphenyl)-2-oxoethane and 2.15 g (0.026 mol) of 1-methylimidazole in approximately 30 ml of diethyl ether was stirred at room temperature for about 19 hours. The reaction solvent was decanted and the resulting brown residue was washed with diethyl ether. The residue was washed with hot acetonitrile and recrystallized twice from acetonitrile/diethyl ether to afford 1.74 g of 1-methyl-3-[2-(3-methylphenyl)-2-oxoethyl]-1H-imidazolium bromide as white needles. (25% yield) mp=185°–187° C.

Analysis calculated for $C_{13}H_{15}BrN_2O$. Theory: C, 52.90; H, 5.12; N, 9.49; Br, 27.07; Found : C, 53.11; H, 5.08; N, 9.43; Br, 26.96.

The following Examples illustrate additional compounds employed in the present invention and were prepared by the general procedures outlined above.

EXAMPLE 11

1-Methyl-3-[2-(2,5-dimethoxyphenyl)-2-oxoethyl]-1H-imidazolium bromide, mp=207°–210° C. dec.

Analysis calculated for $C_{14}H_{17}BrN_2O$. Theory: C, 49.28; H, 5.02; N, 8.21; Br, 23.42; Found: C, 49.05; H, 4.98; N, 8.08; Br, 23.14.

EXAMPLE 12

1-n-Propyl-3-(2-phenyl-2-oxoethyl)-1H-imidazolium chloride, mp=143°–150° C.

Analysis calculated for $C_{14}H_{17}ClN_2O$. Theory: C, 63.51; H, 6.47; N, 10.58; Found: C, 64.81; H, 6.77; N, 9.86.

EXAMPLE 13

1-Methyl-3-[2-(2-methoxyphenyl)-2-oxoethyl]-1H-imidazolium bromide, mp=165°–167° C.

Analysis calculated for $C_{13}H_{15}BrN_2O_2$. Theory: C, 50.18; H, 4.86; N, 9.00; Br, 25.68; Found: C, 49.95; H, 4.97; N, 8.78; Br, 25.92.

EXAMPLE 14

1-Methyl-3-[2-(3,5-dimethoxyphenyl)-2-oxoethyl]-1H-imidazolium bromide, mp=239°–241° C. dec.

Analysis calculated for $C_{14}H_{17}BrN_2O_3$. Theory: C, 49.28; H, 5.02; N, 8.21; Br, 23.42; Found: C, 49.33; H, 4.98; N, 7.97; Br, 23.34.

EXAMPLE 15

1-Methyl-3-[2-(4-ethoxyphenyl)-2-oxoethyl]-1H-imidazolium bromide, mp=143°–146° C.

Analysis calculated for $C_{14}H_{17}BrN_2O_2$. Theory: C, 51.71; H; 5.27; N, 8.61; Br, 24.57; Found: C, 51.49; H, 5.39; N, 8.42; Br, 24.45.

EXAMPLE 16

1-Methyl-3-[2-(3,4-dimethylphenyl)-2-oxoethyl]-1H-imidazolium bromide, mp=163°–165° C.

Analysis calculated for $C_{14}H_{17}BrN_2O$. Theory: C, 54.38; H, 5.54; N, 9.09; Br, 25.84; Found: C, 54.61; H. 5.49; N, 9.17; Br, 25.90.

EXAMPLE 17

1-Methyl-3-[2-(4-methoxyphenyl)-2-oxoethyl]-1H-imidazolium bromide, mp=156°–159° C.

Analysis calculated for $C_{13}H_{15}BrN_2O_2$. Theory: C, 50.18; H, 4.86; N, 9.00; Br, 25.68; Found: C, 49.98; H, 5.11; N, 8.82; Br, 25.95.

EXAMPLE 18

1-Methyl-3-(2-phenyl-2-oxoethyl)-1H-imidazolium chloride, mp=104°–108° C.

Analysis calculated for $C_{12}H_{13}ClN_2O_2$. Theory: C, 60.89; H, 5.53; N, 11.84; Cl, 14.98; Found: C, 59.63; H, 5.35; N, 11.37; Cl, 14.33.

The present invention provides a method for lowering blood glucose levels in mammals comprising administering an effective amount of an imidazolium compound of formula I. The term "effective amount", as defined herein, means the amount of compound necessary to provide a hypoglycemic effect following administration preferably to a mammal susceptible to adult onset diabetes.

The active compounds are effective over a wide dosage range. For example, dosages per day will normally fall within the range of about 0.5 to about 500 mg/kg of body weight. In the treatment of adult humans, the range of about 1.0 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to reduce blood glucose levels in mammals, the compounds may also be administered by a variety of other routes such as the transdermal, subcutaneous, intranasal, intramuscular and intravenous routes.

The compounds employed in the present invention function differently than sulfonylureas and are believed to improve insulin resistance. Therefore, the present compounds are particularly well suited for Type II, or adult onset, diabetics since many of these individuals have sufficient circulating insulin but are resistant to insulin itself. However, the precise mechanism by which the present compounds function is not yet known, and the present invention is not limited by any mode of operation.

As noted above, the compounds of the present invention are preferably orally administered to the subject in question. While it is possible to administer a compound of the invention directly without any formulation, the compounds are preferably employed in the form of a pharmaceutical formulation comprising a pharmaceutically acceptable carrier, diluent or excipient and a compound of the invention. Such compositions will contain from about 0.1 percent to about 90 percent of a present compound.

In making the compositions of the present invention the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propyl-hydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only and are not intended to limit the scope of the invention. The formulations may employ as active compounds any of the pharmaceutical compounds of formula I.

FORMULATION 1

Hard gelatin capsules are prepared using the following ingredients:

|  | Amount Per Capsule | Concentration by Weight (percent) |
| --- | --- | --- |
| 1-Methyl-3-[2-(4-methylphenyl)-2-oxoethyl]-1H—imidazolium bromide | 250 mg | 55.0 |
| Starch dried | 200 mg | 43.0 |
| Magnesium stearate | 10 mg | 2.0 |
|  | 460 mg | 100.0 |

The above ingredients are mixed and filled into hard gelatin capsules in 460 mg quantities.

FORMULATION 2

Capsules each containing 20 mg of medicament are made as follows:

|  | Amount Per Capsule | Concentration by Weight (percent) |
| --- | --- | --- |
| 1-Methyl-3-[2-(3-methoxyphenyl)-2-oxoethyl]-1H—imidazolium bromide | 20 mg | 10.0 |
| Starch | 89 mg | 44.5 |
| Microcrystalline cellulose | 89 mg | 44.5 |
| Magnesium stearate | 2 mg | 1.0 |
|  | 200 mg | 100.0 |

The active ingredient, cellulose, starch and magnesium stearate are blended, passed through a No. 45 mesh U.S. sieve and filled into a hard gelatin capsule.

FORMULATION 3

Capsules each containing 100 mg of active ingredient are made as follows:

|  | Amount Per Capsule | Concentration by Weight (percent) |
| --- | --- | --- |
| 1-Methyl-3-[2-(3-ethoxyphenyl)-2-oxoethyl]-1H—imidazolium bromide | 100 mg | 29.0 |
| Polyoxyethylenesorbitan monooleate | 50 mcg | 0.02 |
| Starch powder | 250 mg | 71.0 |
|  | 350.05 mg | 100.02 |

The above ingredients are thoroughly mixed and placed in an empty gelatin capsule.

FORMULATION 4

Tablets each containing 10 mg of active ingredient are made up as follows:

|  | Amount Per Tablet | Concentration by Weight (percent) |
| --- | --- | --- |
| 1-Methyl-3-(1,1-dimethyl-2-phenyl-2-oxoethyl)-1H—imidazolium bromide | 10 mg | 10.0 |
| Starch | 45 mg | 45.0 |
| Microcrystalline cellulose | 35 mg | 35.0 |
| Polyvinyl pyrrolidone (as 10% solution in water) | 4 mg | 4.0 |
| Sodium carboxymethyl starch | 4.5 mg | 4.5 |
| Magnesium stearate | 0.5 mg | 0.5 |
| Talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5

A tablet formula may be prepared using the ingredients below:

|  | Amount Per Tablet | Concentration by Weight (percent) |
|---|---|---|
| 1-Methyl-3-[2-(4-ethyl-phenyl)-2-oxoethyl]-1H—imidazolium bromide | 250 mg | 38.0 |
| Cellulose microcrystalline | 400 mg | 60.0 |
| Silicon dioxide fumed | 10 mg | 1.5 |
| Stearic acid | 5 mg | 0.5 |
|  | 665 mg | 100.0 |

The components are blended and compressed to form tablets each weighing 665 mg.

FORMULATION 6

Suspensions each containing 5 mg of medicament per 5 ml dose are made as follows:

|  | per 5 ml of suspension |
|---|---|
| 1-Methyl-3-[2-(2-methylphenyl)-2-oxoethyl]-1H—imidazolium bromide | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

FORMULATION 7

An aerosol solution is prepared containing the following components:

|  | Concentration by Weight (percent) |
|---|---|
| 1-Methyl-3-(1-methyl-2-oxo-2-phenylethyl)-1H—imidazolium bromide | 0.25 |
| Ethanol | 29.75 |
| Propellant 22 (Chlorodifluoromethane) | 70.00 |
|  | 100.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

The hypoglycemic activity of the present compounds was determined by testing the efficacy of formulations of the compounds in vivo in viable yellow obese-diabetic mice. The test procedure is described in detail below.

EXPERIMENT

Test formulations were prepared by dissolving the test compound in a saline solution containing 2% Emulphor (a polyoxyethylated vegetable oil surfactant from GAF Corp.) to provide a dose level of 100 mg/kg. Each test formulation was administered to six viable yellow obese-diabetic mice by gavage. Evaluations of the blood glucose level were recorded at 0, 2 and 4 hours following administration. A mean was taken of the 6 values and the data is reported below in Table 1 below.

TABLE 1

Blood Glucose Levels in Obese-Diabetic Mice

| Example No. of Compound Tested | Hours after administration | Percent Blood Glucose | Probability |
|---|---|---|---|
| 1 | 0 | 100 |  |
|  | 2 | 80 ± 3 | 0.0010 |
|  | 4 | 88 ± 8 | 0.1439 |
| 2 | 0 | 100 |  |
|  | 2 | 63 ± 4 | 0.0006 |
|  | 4 | 76 ± 4 | 0.0013 |
| 3 | 0 | 100 |  |
|  | 2 | 66 ± 9 | 0.0138 |
|  | 4 | 89 ± 4 | 0.0383 |
| 4 | 0 | 100 |  |
|  | 2 | 84 ± 5 | 0.0203 |
|  | 4 | 78 ± 8 | 0.0491 |
| 5 | 0 | 100 |  |
|  | 2 | 77 ± 5 | 0.0135 |
|  | 4 | 88 ± 6 | 0.1478 |
| 6 | 0 | 100 |  |
|  | 2 | 93 ± 6 | 0.2633 |
|  | 4 | 95 ± 6 | 0.3490 |
| 7 | 0 | 100 |  |
|  | 2 | 70 ± 6 | 0.0077 |
|  | 4 | 61 ± 7 | 0.0062 |
| 8 | 0 | 100 |  |
|  | 2 | 75 ± 5 | 0.0096 |
|  | 4 | 69 ± 8 | 0.0126 |
| 9 | 0 | 100 |  |
|  | 2 | 77 ± 4 | 0.0054 |
|  | 4 | 76 ± 5 | 0.0076 |
| 10 | 0 | 100 |  |
|  | 2 | 78 ± 5 | 0.0224 |
|  | 4 | 73 ± 7 | 0.0214 |
| 11 | 0 | 100 |  |
|  | 2 | 78 ± 5 | 0.0031 |
|  | 4 | 86 ± 7 | 0.0830 |
| 12 | 0 | 100 |  |
|  | 2 | 79 ± 7 | 0.0482 |
|  | 4 | 79 ± 7 | 0.0207 |
| 13 | 0 | 100 |  |
|  | 2 | 83 ± 9 | 0.0832 |
|  | 4 | 101 ± 11 | 0.7976 |
| 14 | 0 | 100 |  |
|  | 2 | 90 ± 5 | 0.1043 |
|  | 4 | 108 ± 5 | 0.1696 |
| 15 | 0 | 100 |  |
|  | 2 | 78 ± 9 | 0.0658 |
|  | 4 | 103 ± 5 | 0.6756 |
| 16 | 0 | 100 |  |
|  | 2 | 83 ± 4 | 0.0049 |
|  | 4 | 95 ± 4 | 0.2686 |
| 17 | 0 | 100 |  |
|  | 2 | 79 ± 3 | 0.0010 |
|  | 4 | 93 ± 7 | 0.2804 |
| 18 | 0 | 100 |  |
|  | 2 | 74 ± 4 | 0.0074 |
|  | 4 | 71 ± 7 | 0.0099 |

Certain of the compounds were also tested in Type II diabetic rats and were found to have the ability to lower blood glucose levels in these mammals as well.

We claim:

1. A method for lowering blood glucose levels in mammals comprising administering an effective amount of a compound of the formula

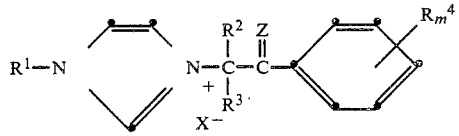

wherein:
R$^1$ is C$_1$–C$_4$ alkyl;
R$^2$ and R$^3$ independently are hydrogen or C$_1$–C$_4$ alkyl;
each R$^4$ independently is —OR$^5$, —NR$^6$R$^7$, C$_1$–C$_4$ alkyl, C$_1$–C$_4$ alkoxy or C$_1$–C$_4$ alkylthio;
R$^5$ is hydrogen or

R$^6$ is hydrogen, C$_1$–C$_4$ alkyl or

R$^7$ is hydrogen or C$_1$–C$_4$ alkyl;
each R$^8$ independently is C$_1$–C$_4$ alkyl or phenyl;
Z is oxygen or sulfur;
X is a therapeutically acceptable anion; and
m is 0, 1 or 2.

2. A method of claim 1 wherein R$^1$ is methyl.

3. A method of claim 2 wherein both R$^2$ and R$^3$ are hydrogen.

4. The method of claim 3 wherein the compound is 1-methyl-3-[2-(4-methylphenyl)-2-oxoethyl]-1H-imidazolium bromide.

5. The method of claim 3 wherein the compound is 1-methyl-3-[2-(3-methoxyphenyl)-2-oxoethyl]-1H-imidazolium bromide.

6. The method of claim 3 wherein the compound is 1-methyl-3-[2-(3-ethoxyphenyl)-2-oxoethyl-1H-imidazolium bromide.

7. The method of claim 3 wherein the compound is 1-methyl-3-[2-(4-ethylphenyl)-2-oxoethyl]-1H-imidazolium bromide.

8. The method of claim 3 wherein the compound is 1-methyl-3-[2-(2-methylphenyl)-2-oxoethyl]-1H-imidazolium bromide.

9. The method of claim 3 wherein the compound is 1-methyl-3-[2-(2,4-dimethylphenyl)-2-oxoethyl]-1H-imidazolium bromide.

10. The method of claim 3 wherein the compound is 1-methyl-3-[2-(3-methylphenyl)-2-oxoethyl]-1H-imidazolium bromide.

11. The method of claim 3 wherein the compound is 1-methyl-3-[2-(2,5-dimethoxyphenyl)-2-oxoethyl]-1H-imidazolium bromide.

12. A method of claim 2 wherein one of R$^2$ and R$^3$ hydrogen and the other is methyl.

13. A method of claim 2 wherein R$^2$ and R$^3$ are both methyl.

14. A pharmaceutical formulation useful for lowering blood glucose levels in mammals comprising a pharmaceutically acceptable carrier, diluent or excipient and an effective amount of a compound of the formula

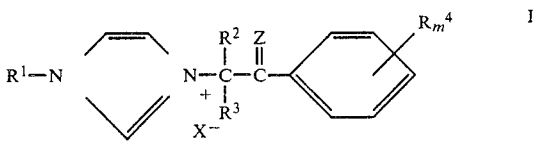

wherein:
r$^1$ is C$_1$–C$_4$ alkyl;
R$^2$ and R$^3$ independently are hydrogen or C$_1$–C$_4$ alkyl;
each R$^4$ independently is —OR$^5$, —NR$^6$R$^7$, C$_1$–C$_4$ alkyl, C$_1$–C$_4$ alkoxy or C$_1$–C$_4$ alkylthio;
R$^5$ is hydrogen or

R$^6$ is hydrogen, C$_1$–C$_4$ alkyl or

R$^7$ is hydrogen or C$_1$–C$_4$ alkyl;
each R$^8$ independently is C$_1$–C$_4$ alkyl or phenyl;
Z is oxygen or sulfur;
X is a therapeutically acceptable anion; and
m is 1 or 2.

15. A formulation of claim 14 wherein R$^1$ is methyl.

16. A formulation of claim 15 wherein both R$^2$ and R$^3$ are hydrogen.

17. The formulation of claim 16 wherein the compound is 1-methyl-3-[2-(4-methylphenyl)-2-oxoethyl]-1H-imidazolium bromide.

18. The formulation of claim 15 wherein the compound is 1-methyl-3-[2-(3-methoxyphenyl)-2-oxoethyl]-1H-imidazolium bromide.

* * * * *

UNITED STATES PATENT AND TRADEMARK OFFICE
CERTIFICATE OF CORRECTION

PATENT NO. : 4,609,670

DATED : September 2, 1986

INVENTOR(S) : Samuel J. Dominianni et al.

It is certified that error appears in the above-identified patent and that said Letters Patent are hereby corrected as shown below:

Column 15, line 13, "$-NR^{G}R^{7}$" should read -- $-NR^{6}R^{7}$ -- .

Column 16, line 24, "$r^{1}$" should read -- $R^{1}$ -- .

Signed and Sealed this

Tenth Day of November, 1987

Attest:

DONALD J. QUIGG

*Attesting Officer*  *Commissioner of Patents and Trademarks*